United States Patent [19]

Chiba et al.

[11] 4,304,652

[45] Dec. 8, 1981

[54] DEVICE FOR DETECTION OF AIR/FUEL RATIO FROM OXYGEN PARTIAL PRESSURE IN EXHAUST GAS

[75] Inventors: Masao Chiba, Chigasaki; Takeshi Fujishiro, Yokosuka, both of Japan

[73] Assignee: Nissan Motor Company, Limited, Yokohama, Japan

[21] Appl. No.: 157,183

[22] Filed: Jun. 6, 1980

[30] Foreign Application Priority Data

Jun. 12, 1979 [JP] Japan ................................. 54-73012

[51] Int. Cl.³ ............................................ G01N 27/58
[52] U.S. Cl. .................................................. 204/195 S
[58] Field of Search ............................ 204/195 S, 1 S

[56] References Cited

U.S. PATENT DOCUMENTS

| | | | |
|---|---|---|---|
| 3,719,564 | 3/1973 | Lilly et al. | 204/1 T |
| 3,738,341 | 6/1973 | Loos | 204/195 S UX |
| 4,005,001 | 1/1977 | Pebler | 204/195 S |
| 4,207,159 | 6/1980 | Kimura et al. | 204/195 S |
| 4,224,113 | 9/1980 | Kimura et al. | 204/1T |

*Primary Examiner*—G. L. Kaplan
*Attorney, Agent, or Firm*—Schwartz, Jeffery, Schwaab, Mack, Blumenthal & Koch

[57] ABSTRACT

A device having a probe of the oxygen concentration cell type to be disposed in a combustion gas to detect actual air/fuel ratio values of an air-fuel mixture subjected to combustion. The probe has a gas impermeable layer of a solid electrolyte such as zirconia, a porous reference electrode layer made of a catalytic material such as platinum and formed on the solid electrolyte layer, a porous gas-diffusion layer covering the reference electrode layer and a porous and noncatalytic measurement electrode layer formed on the solid electrolyte layer so as to be spaced from the reference electrode layer. A DC power supply is connected to the probe to force a constant current of an adequate intensity to flow through the solid electrolyte layer between the two electrode layers. Depending on the direction of the current flow, an output voltage of this device becomes indicative of air/fuel ratio values above or below the stoichiometric air/fuel ratio.

17 Claims, 22 Drawing Figures

4,304,652

DEVICE FOR DETECTION OF AIR/FUEL RATIO FROM OXYGEN PARTIAL PRESSURE IN EXHAUST GAS

BACKGROUND OF THE INVENTION

This invention relates to a device for detecting an actual air/fuel ratio of an air-fuel mixture subjected to combustion in a combustor, such as the combustion chambers of an internal combustion engine, based on the magnitude of an oxygen partial pressure in the combustion gas exhausted from the combustor.

In recent automobiles, one of the popularized methods of sufficiently reducing the emission of HC, CO and NOx is to use a three-way catalyst which catalyzes both reduction of NOx and oxidation of HC and CO and an electronically controlled fuel injection system to minutely control the air/fuel ratio so as to maintain a specific air/fuel ratio at which the three-way catalyst exhibits the highest conversion efficiency, and in many cases it is intended to maintain a stoichiometric air/fuel ratio, that is, about 14.5 in gasoline engines. In this method it is usual to perform closed-loop control of the air/fuel ratio by the use of an oxygen sensor installed in the exhaust system to detect a change in the concentration of oxygen in the exhaust gas as an indication of a change in the air/fuel ratio of an air-fuel mixture actually supplied to the engine, because it is more practical to provide an oxygen sensor in the exhaust system than in the intake system of the engine.

An oxygen sensor prevailing for this purpose is of the concentration cell type having a layer of an oxygen ion conductive solid electrolyte, such as zirconia stabilized with calcia, a measurement electrode layer porously formed on one side of the solid electrolyte layer and a reference electrode layer formed on the other side. This oxygen sensor is designed such that the reference electrode layer is exposed to air while the measurement electrode layer is exposed to an exhaust gas and generates an electromotive force the magnitude of which depends on the difference between a reference oxygen partial pressure in air and an oxygen partial pressure in the exhaust gas. When the air/fuel ratio of a mixture supplied to the engine changes across a stoichiometric air/fuel ratio, a great and sharp change is exhibited in the magnitude of the electromotive force which the sensor generates. Accordingly this type of oxygen sensor is suitable for application to engines to be operated with a stoichiometric or approximately stoichiometric air-fuel mixture. From an industrial point of view, however, this type of oxygen sensor is rather low in productivity and difficult to achieve desirable size reduction because of design restrictions placed on it by the necessity of introducing air to the reference electrode layer.

An advanced oxygen sensing device of the concentration cell type is proposed in U.S. patent application Ser. No. 12,763 filed Feb. 16, 1979, now U.S. Pat. No. 4,207,159. This device has a gas permeable porous layer of a solid electrolyte, a porous and film-like measurement electrode layer on one side of the solid electrolyte layer, a reference electrode layer on the other side and a shield layer formed so as to cover the reference electrode layer entirely. The two electrode layers are usually made of platinum, and, as a primary feature of this device, a DC power supply is connected to the two electrode layers to force an electric current to flow through the solid electrolyte layer between the two electrode layers while the measurement electrode layer is exposed to an exhaust gas. The flow of the current between the two electrode layers causes migration of oxygen ions through the solid electrolyte layer and proceeding of electrolytic reactions between oxygen ions and oxygen molecules at the surfaces of the respective electrode layers, and as a result a reference oxygen partial pressure is established at the interface between the reference electrode layer and the solid electrolyte layer. An electromotive force measured between the reference and measurement electrode layers of this device exhibits a sharp change in its magnitude when the air/fuel ratio of an air-fuel mixture from which the exhaust gas is produced changes across the stoichiometric ratio. (A more detailed description about the function of this device will be given hereinafter.) Accordingly, this device is useful for engines to be operated with a stoichiometric air-fuel mixture and advantageous in that there is no need of using an external oxygen source to provide a reference oxygen partial pressure and that the device can be made small in size and produced easily.

Meanwhile, the development of so-called lean-burn engines has been in progress with the view of attaining a maximal thermal efficiency. Also, so-called rich-burn engines have attracted attention because of the possibility of achieving a very high mechanical efficiency and have already been put into practice when recirculation of exhaust gas is employed as a measure of decreasing the emission of NOx. Accordingly there is a demand for an oxygen sensor which is to be used in exhaust gases and enables detection not only of a stoichiometric air/fuel ratio but also air/fuel ratios either above or below the stoichiometric ratio.

According to U.S. patent application Ser. No. 28,747 filed Apr. 10, 1979, now U.S. Pat. No. 4,224,113, it is possible to detect air/fuel ratio values of either a lean mixture or a rich mixture supplied to a combustion engine by using the above described device of U.S. Pat. No. 4,207,159 and by adequately determining the intensity of the electric current forced to flow through the solid electrolyte layer. More particularly, when the current is made to flow from the measurement electrode layer towards the reference electrode layer of the device and the current intensity is below a certain critical value, the output voltage of the device in the exhaust gas remains negligibly low while a rich mixture is supplied to the engine but abruptly rises to a maximal level when the air/fuel ratio reaches the stoichiomeric ratio and, when a lean mixture is supplied to the engine, exhibits a gradual lowering as the air/fuel ratio supplied to the engine becomes higher. Accordingly it is possible to detect a stoichiometric air/fuel ratio and higher air/fuel ratios by using the device in this manner. When a current of an intensity below a certain critical value is made to flow in the reverse direction, the output voltage of the device remains negligibly low while a lean mixture is supplied to the engine, abruptly rises to a maximal level at the stoichiometric air/fuel ratio and, when a rich mixture is supplied to the engine, exhibits a gradual lowering as the air/fuel ratio decreases from the stoichiometric ratio. In this case, therefore, a stoichiometric air/fuel ratio and lower air/fuel ratios can be detected by this device.

However, the air/fuel ratio detection method of U.S. Pat. No. 4,224,113 is inconvenient in that an output voltage value corresponding to a certain air/fuel ratio value of a lean mixture (or a rich mixture) appears also when the output voltage undergoes a sharp change upon arrival of the air/fuel ratio at the stoichiometric ratio. Accordingly a closed-loop air/fuel ratio control system based on this method needs to include certain means for judging whether a measured value of the output voltage indicates the stoichiometric air/fuel ratio or a higher (or lower) air/fuel ratio or means for taking out only output voltage values in the inclined portion of the (air/fuel ratio)-to-(output voltage) characteristic curve. Of course the need for the provision of such means results in undersirable complication of the control system.

SUMMARY OF THE INVENTION

It is an object of the present invention to provide a device to detect actual air/fuel ratio values of an air-fuel mixture subjected to combustion in a combustor, such as an automotive internal combustion engine, based on the magnitude of an oxygen partial pressure in a combustion gas exhausted from the combustor, which device is simple in construction, can be made small in size and has the capability of accurately and definitely indicating either air/fuel ratios above a stoichiometric air/fuel ratio or air/fuel ratios below the stoichiometric ratio.

An air/fuel ratio detection device according to the invention comprises an oxygen sensing element which can be disposed in a combustion gas. This element comprises a layer of an oxygen ion conductive solid electrolyte having a dense and gas impermeable structure, a gas permeable porous first electrode layer which is formed on the solid electrolyte layer and made of a conducting and catalytic material which catalyzes oxidation reactions of combustible substances contained in the combustion gas, a porous gas-diffusion layer formed on the first electrode layer and a gas permeable porous second electrode layer which is formed on the solid electrolyte layer so as to be spaced from the first electrode layer and made of a conducting material which does not catalyze the aforementioned oxidation reactions. The air/fuel ratio detection device further comprises a constant current DC power supply which is electrically connected to the first and second electrode layers of the oxygen sensing element to force a constant DC current to flow through the solid electrolyte layer between the first and second electrode layers while the oxygen sensing element is disposed in the combustion gas. The intensity and the direction of flow of the DC current are determined such that an output voltage developed across the first and second electrode layers varies in dependence on the air/fuel ratio of an air-fuel mixture, from which the combustion gas is produced, when the air/fuel ratio varies on one side of the stoichiometric air/fuel ratio but remains substantially constantly at a maximal level when the air/fuel ratio varies on the other side of the stoichiometric ratio.

Platinum is preferable as the catalytic material for the first electrode layer.

To detect air/fuel ratios above the stoichiometric ratio, the DC current is made to flow from the second electrode layer towards the first electrode layer. In this case the output voltage remains at a maximal level if the air/fuel ratio is below the stoichiometric ratio inclusive, and therefore an output voltage value below the maximal level indicates only one definite air/fuel ratio value above the stoichiometric ratio. To detect air/fuel ratios below the stoichiometric ratio, the DC current is made to flow from the first electrode layer towards the second electrode layer. In this case the output voltage remains at a maximal level if the air/fuel ratio is above the stoichiometric ratio inclusive, and therefore an output voltage value below the maximal level indicates only one definite air/fuel ratio value below the stoichiometric ratio.

Thus, the device according to the invention is applicable to either lean-burn engines or rich-burn engines as an element of a closed-loop air/fuel ratio control system without necessitating complication of the control system. Besides, this device is simple in construction, high in productivity and can be made very small in size.

DESCRIPTION OF THE PREFERRED EMBODIMENTS

Figure 1:
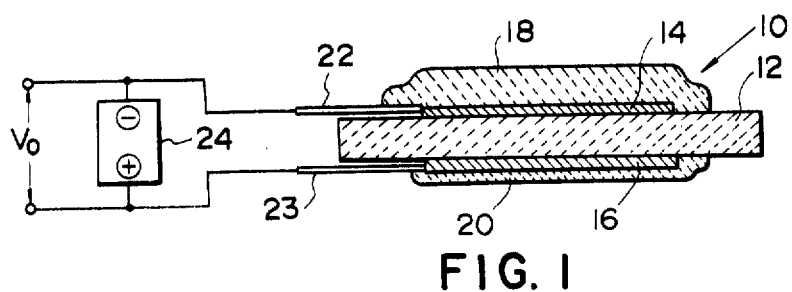
FIG. 1 is a schematic and sectional illustration of an air/fuel ratio detecting device as an embodiment of the present invention.

FIG. 1 shows an air/fuel ratio detecting device embodying the present invention. Principally, this device is a combination of an oxygen sensing element 10 and a DC power supply 24 of a constant current type. The oxygen sensing element 10 has a layer 12 of an oxygen ion conductive solid electrolyte in the form of a rigid plate thick enough to serve as a structurally basic member of this element 10. This solid electrolyte layer 12 is made to have a dense and tight structure so as not to allow oxygen molecules to permeate therethrough, though oxygen ions can migrate through this layer 12. A thin, film-like reference electrode layer 14 of platinum is formed on one side of the solid electrolyte plate 12, and a thin, film-like measurement electrode layer 16 of a noncatalytic material is formed on the other side of the plate 12. These two electrode layers 14 and 16 are both made to have a microscopically porous and gas permeable structure. The reference electrode layer 14 is substantially entirely covered with a porous and sufficiently thick gas-diffusion layer 18 of a heat-resistant material, while the measurement electrode layer 16 is substantially entirely covered with a porous protective layer 20 of a heat-resistant material. Indicated at 22 and 23 are lead terminals attached to the reference and measurement electrode layers 14 and 16, respectively.

The DC power supply 24 is of the type capable of supplying a constant current and connected to leads 22 and 23 of the oxygen sensing element 10 to force a predetermined intensity of DC current to flow through the solid electrolyte layer 12 between the two electrode layers 14 and 16 in a predetermined direction (in the illustrated case, from the measurement electrode layer 16 towards the reference electrode layer 14) during use of this device. In practice the current supply circuit in FIG. 1 includes a switch, which is omitted from the illustration. When the oxygen sensing element 10 of this device is disposed in a combustion gas such as an exhaust gas of an internal combustion engine, an output voltage $V_0$ measured across the positive and negative terminals of the DC power supply 24 represents an electromotive force which is generated by an oxygen concentration cell which the element 10 constitutes and depends on the magnitude of a difference between an oxygen partial pressure at the reference electrode layer 14 and another oxygen partial pressure at the measurement electrode layer 16.

The material of the solid electrolyte layer 12 is selected from oxygen ion conductive solid electrolyte materials known as useful for conventional oxygen sensors of the concentration cell type. Some examples are $ZrO_2$ stabilized with $Y_2O_3$, CaO or MgO; $Bi_2O_3$ stabilized with $Y_2O_3$ or $Nb_2O_5$; $ThO_2$-$Y_2O_3$ system; and $CaO$-$Y_2O_3$ system. The solid electrolyte layer 12 can be made, for example, by sintering of a press-molded powder material or sintering of a so-called green sheet obtained by molding or extrusion of a wet composition of which the principal component is a powdered solid electrolyte material.

Platinum is particularly preferable as the material for the reference electrode layer 14 which is required to exhibit a catalytic activity on oxidation reactions of hydrocarbons and carbon monoxide, but if desired a choice may be made among other metals of the platinum group and various alloys of platinum group metals.

The material for the measurement electrode layer 16 is required not to exhibit a catalytic activity on oxidation reactions of hydrocarbons, carbon monoxide, etc. Examples of useful conducting materials are certain metals such as Au and Ag; SiC; electronically conducting metal oxides such as $SnO_2$, $V_2O_5$ and PbO which may be admixed with $Al_2O_3$ or the like; and oxide semiconductors of the Perovskite structure such as $LaCrO_3$, $LaNiO_3$ and $SmCoO_3$ respectively with added Ca, Zr, Mg and/or Sr.

Each electrode layer 14, 16 can be formed on the solid electrolyte layer 12 either by a physical deposition technique such as sputtering or vacuum evaporation or by printing of a conductive paste (containing a powdered electrode material dispersed in an organic medium) and subsequent firing of the paste-applied solid electrolyte layer 12.

For the porous gas-diffusion layer 18 and the porous protective layer 20, use may be made of a heat-resistant and electrically nonconducting material such as alumina, spinel, magnesia or calcium zirconate ($ZrO_2$-CaO). Each of these porous layers 18 and 20 can be formed, for example, by plasma spraying or by printing of a paste and subsequent firing.

Figure 2A:
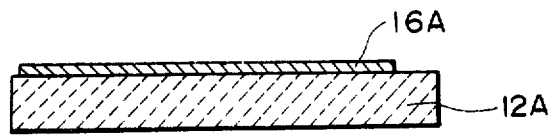
FIGS. 2(A) to 2(E) illustrate an exemplary process of producing the device of FIG. 1.
Figure 2B:
Figure 2C:
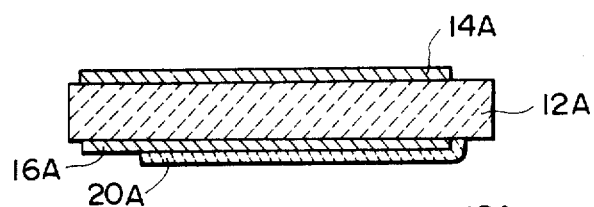
Figure 2D:
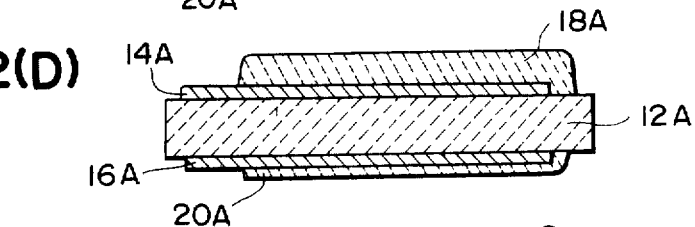
Figure 2E:
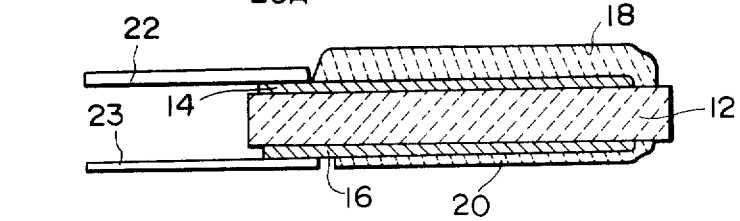

By way of example, a process of producing the oxygen sensing element 10 of FIG. 1 will be described with reference to FIGS. 2(A) to 2(E). First, a paste containing fine particles of Au and SiC is applied onto one side of a green or unfired plate 12A of $ZrO_2$, containing $Y_2O_3$ as a stabilizing component, by a screen printing technique so as to form a thin layer 16A of the conductive paste as shown in FIG. 2(A). After drying of the printed paste layer 16A at about 150° C. for about 1 hr, a paste containing 30-40 $\mu$m particles of $Al_2O_3$ is applied onto the same side of the zirconia plate by a screen-printing technique so as to cover the conductive paste layer 16A almost entirely, as indicated at 20A in FIG. 2(B), leaving only a marginal region for attachment of a lead terminal. The resultant alumina paste layer 20A is dried at about 150° C. for about 1 hr. Then a platinum paste is applied onto the other side of the plate 12A by screen-printing to form a thin paste layer 14A as shown in FIG. 2(C), followed by drying at about 150° C. for about 1 hr. Next, as indicated at 18A in FIG. 2(D), a paste containing about 0.5 $\mu$m particles of $Al_2O_3$ (or $ZrO_2$-CaO) is printed onto the same side of the plate 12A to cover the platinum paste layer 14A almost entirely, leaving only a marginal region for attachment of a lead terminal. To make the resultant alumina layer 18A about 20 $\mu$m thick, screen-printing of the alumina paste is repeated several times, each time followed by drying at about 150° C. for about 1 hr. Thereafter the pastecoated plate 12A in the state of FIG. 2(D) is fired in air at a temperature of 1450° C. to achieve sintering of the plate 12A and the four layers 14A, 16A, 18A, 20A coated thereon. Referring to FIG. 2(E), as the result the green plate 12A turns into a rigid plate 12 of $ZrO_2$-$Y_2O_3$ having a dense and gas impermeable structure, while the two inner layers 16A and 14A respectively turn into gas permeable porous measurement and reference electrode layers 16 and 14, and the outer layers 18A and 20A respectively turn into sufficiently porous gas-diffusion and protective layers 18 and 20. Finally, platinum wires 22 and 23 to serve as lead terminals are attached to the reference and measurement electrode layers 14 and 16 by parallel gap welding (or by resistance welding). Alternatively, the platinum wires 22 and 23 may be provisionally attached to the unfired conductive layers 14A and 16A in the state of FIG. 2(D) by using a platinum paste as an adhesive and establishing a firm bonding by sintering of this adhesive during the aforementioned firing of the element of FIG. 2(D).

Figure 3A:
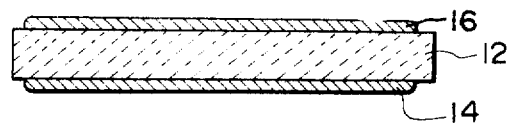
FIGS. 3(A) to 3(C) illustrate a partial modification of the process of FIGS. 2(A)-2(E)
Figure 3B:
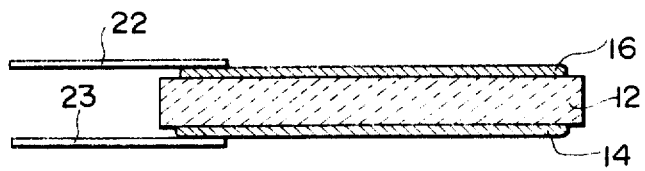
Figure 3C:
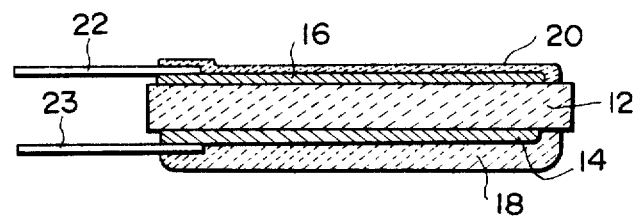

FIGS. 3(A) to 3(C) illustrate a modification of the above described manufacturing process. In this case the process starts by the employment of an already sintered plate 12 of a solid electrolyte. As shown in FIG. 3(A), the porous reference electrode layer 14 of platinum and the porous measurement electrode layer 16 of a noncatalytic electrode material are formed respectively on the front and back sides of the solid electrolyte plate 12 either by sputtering or by vacuum evaporation. Alternatively, these electrode layers 14 and 16 may be formed each by the steps of printing a suitable conductive paste onto the plate 12, drying the printed paste layer and then firing the coated substrate 12 at 900-1000° C. Then lead terminals 22 and 23 are welded to the two electrode layers 14 and 16 as shown in FIG. 3(B). Thereafter the gas-diffusion layer 18 on the reference electrode layer 14 and the protective layer 20 on the measurement electrode layer 16 are formed, as shown in FIG. 3(C), each by plasma spraying.

Figure 4:
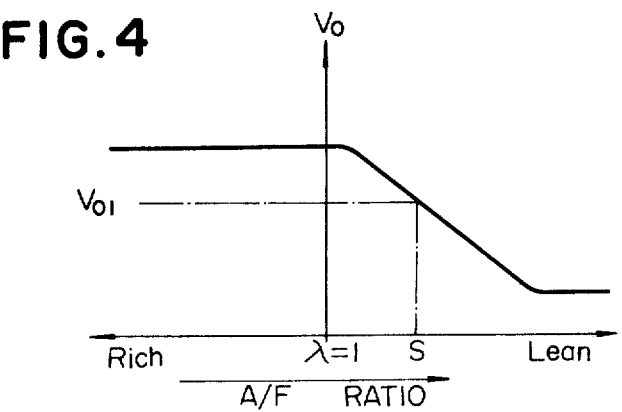
FIGS. 4 and 5 are graphs for the explanation of two different types of output characteristics the device of FIG. 1 can be made to exhibit in an exhaust gas of an internal combustion engine.

The output characteristic of the device of FIG. 1, with the oxygen sensing element 10 disposed in an exhaust gas of an internal combustion engine, more specifically the relationship between the aforementioned output voltage $V_o$ and the air/fuel ratio of an air-fuel mixture from which the exhaust gas was produced, will be explained first with reference to FIG. 4.

The output characteristic of this device is determined primarily by the direction of the electric current kept flowing between the reference and measurement electrode layers 14 and 16. At first the explanation is concerned with a case where the current is made to flow through the solid electrolyte layer 12 from the measurement electrode layer 16 towards the reference electrode layer 14.

In the exhaust gas, the magnitude of the oxygen partial pressure is at the level of $10^{-2}$ to $10^{-3}$ atm whether the engine is operated with a fuel-rich mixture or a lean mixture. The exhaust gas contains certain amounts of combustible gaseous substances such as hydrocarbons (HC) and carbon monoxide (CO), and the total amount of these substances exhibits a sudden and considerable decrease when the air/fuel ratio of the mixture supplied to the engine increases across the stoichiometric air/fuel ratio (about 14.5 for gasoline engines), that is, when the excess air factor $\lambda$ becomes greater than 1.0. However, the amount of these substances exhibits a rapid and considerable increase when the air/fuel ratio lowers across the stoichiometric ratio.

While the engine is operated with a rich mixture, relatively large amounts of HC and CO contained in the exhaust gas diffuse through the microscopic holes in the porous gas-diffusion layer 18 of the oxygen sensing element 10 to reach the reference electrode layer 14 and undergo oxidation reactions due to the catalytic activity of this electrode layer 14. This means consumption of a considerable portion of oxygen contained in the exhaust gas at the surface of the reference electrode layer 14. Therefore, an oxygen partial pressure Po(I) at the interface between the reference electrode layer 14 and the solid electrolyte layer 12 becomes of a considerably small magnitude such as $10^{-15}$ to $10^{-30}$ atm.

The exhaust gas arrives at the measurement electrode layer 16 too through the porous protective layer 20. Since the measurement electrode layer 16 does not catalyze oxidation of HC and CO, an oxygen partial pressure Po(II) at the interface between this electrode layer 16 and the solid electrolyte layer 12 does not differ from the oxygen partial pressure in the exterior exhaust gas, that is, Po(II) is $10^{-2}$ to $10^{-3}$ atm. Thus, there arises a great difference between Po(I) and Po(II). The magnitude of this difference becomes still greater for the additional reason that migration of oxygen ions through the solid electrolyte layer 12 from the reference electrode layer 14 to the measurement electrode layer 16, that is, reverse to the direction of flow of the current through the solid electrolyte layer 12, causes further lowering of an oxygen partial pressure at the reference electrode layer 14 and further rise of the oxygen partial pressure at the measurement electrode layer 16.

Consequently, while the engine is operated with a rich mixture, the output voltage $V_o$ of the device of FIG. 1 remains at a constant and maximally high value given by the following equation irrespective of the value of air/fuel ratio of the rich mixture:

$$V_o = \frac{RT}{4F} \ln \frac{Po(I)}{Po(II)}$$

where R is the gas constant, F is the Faraday constant, and T is the absolute temperature. In practice, this constant value of $V_o$ is about one volt.

When the engine is operated with a lean mixture, the exhaust gas becomes to contain very decreased amounts of combustible substances such as HC and CO. Even under such a condition, the magnitude of the oxygen partial pressure Po(II) at the noncatalytic measurement electrode layer 16 remains at the level of $10^{-2}$ to $10^{-3}$ atm. However, the oxygen partial pressure Po(II) at the reference electrode layer 14 becomes gradually higher and gradually nears the value of Po(I) as the air/fuel ratio of the lean mixture becomes higher for the following reason.

Because of rapid and great decrease in the amounts of HC and CO in the exhaust gas when the air/fuel ratio exceeds the stoichiometric ratio, the consumption of oxygen in oxidation reactions of HC and CO at the surface of the reference electrode layer 14 becomes of little significance, so that the consumption of oxygen at this electrode layer 14 in the formation of oxygen ions which migrate through the solid electrolyte layer 12 towards the measurement electrode layer 16 becomes appreciable. The microscopic holes in the porous gas-diffusion layer 18 are not uniform in their diameter and effective length. In other words, a group of holes relatively large in diameter and easy for oxygen gas to diffuse therethrough and another group of holes relatively small in diameter and difficult for oxygen gas to diffuse therethrough are distributed quite randomly. Since the rate of consumption of oxygen in the forming of oxygen ions at the reference electrode layer 14 is constant, the diffusion of oxygen gas through these two groups of microscopic holes in the gas-diffusion layer 18 at considerably different diffusion rates results in production of relatively high oxygen partial pressures in some areas of the reference electrode layer 14 and relatively low oxygen partial pressures in the remaining areas of this electrode layer 14. Therefore, an average value of such different oxygen partial pressures becomes the magnitude of oxygen partial pressure Po(I) at the reference electrode layer 14 considered macroscopically, but the oxygen sensing element 10 under this condition can be regarded as an assembly of an immense number of microscopic concentration cells each corresponding to a microscopic hole in the gas-diffusion layer 18. The output voltage $V_o$ of the device can be considered to be an average of electromotive forces generated by the microscopic concentration cells. The proportion of the relatively low oxygen partial pressure areas of the reference electrode layer 14 to the relatively high oxygen partial pressure areas, that is, the proportion of the micro-cells generating relatively large magnitudes of EMF to the micro-cells generating relatively small magnitudes of EMF, gradually decreases as the air/fuel ratio of the lean mixture becomes higher. Accordingly the output voltage $V_o$ of the device gradually lowers as the air/fuel ratio increases. When the air/fuel ratio exceeds a certain value, the oxygen partial pressure Po(I) at the reference electrode layer 14 becomes of the same magnitude as the oxygen partial pressure Po(II) at the measurement electrode layer 16, so that the oxygen sensing element 10 no longer generates an appreciable electromotive force.

Thus, the magnitude of the output voltage $V_o$ of this device exhibits a linear change in response to a change in the air/fuel ratio of the lean mixture within a practically useful range, but in exhaust gases produced from a rich mixture, constantly remains at a saturated value. Accordingly, an output voltage value $V_{o1}$ below the saturated value indicates only one definite value $S_1$ of the air/fuel ratio.

As will be understood from the foregoing explanation, the intensity of the constant current forced to flow between the two electrode layers 14 and 16 should be determined adequately. If the current intensity is too small, the application of the current has no effect. If the current intensity is too high, there occurs too much consumption of oxygen at the reference electrode layer 14 in the form of oxygen ions compared with the quantity of oxygen gas diffused through the gas-diffusion layer 18 with the result that the oxygen partial pressure Po(I) at the reference electrode layer 14 exhibits little rise, meaning that the output voltage $V_o$ remains almost constant, even though the air/fuel ratio of the lean mixture increases. There is a critical current intensity above which the magnitude of the output voltage $V_o$ of the device becomes substantially constant regardless of changes in the air/fuel ratio of the lean mixture, and accordingly it is necessary to adjust the DC power supply 24 so as to supply a constant current the intensity of which is below the critical current intensity. Usually the critical current intensity is in the range from about 3 $\mu$A to about 20 $\mu$A. The inclination of the output characteristic curve of FIG. 4 can be varied by the selection of the intensity of the current forced to flow between the two electrodes 14 and 16.

Figure 5:
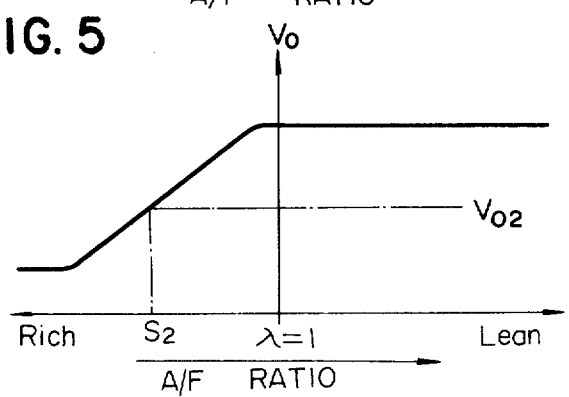

By inverting the polarity in the connection of the DC power supply 24 to the reference and measurement electrode layers 14 and 16 to force a constant current to flow from the reference electrode layer 14 to the measurement electrode layer 16, the device of FIG. 1 can be made to exhibit an output characteristic as shown in FIG. 5. In this case, the output voltage $V_o$ remains constantly at a maximal level while the engine is operated with a lean mixture, but when a rich mixture is employed the output voltage $V_o$ undergoes a gradual lowering as the air/fuel ratio becomes lower. The reason will be understood from the previous explanation concerning FIG. 4. Therefore, an output voltage value $V_{o2}$ below the maximal level indicates only one definite value $S_2$ of the air/fuel ratio below the stoichiometric ratio.

Thus, the device of FIG. 1 can be applied to either lean-burn engines or rich-burn engines merely by selectively determining the polarity in the connection of the DC power supply 24 to the oxygen sensing element 10. In either case, the use of this device allows simplification of a closed-loop air/fuel ratio control system since an output voltage value of this device corresponds to only one definite value of the air/fuel ratio.

For comparison, the function of an air/fuel ratio detecting device disclosed in the aforementioned two U.S. Patents will be explained with reference to FIGS. 6 and 7.

An oxygen sensing element or probe 30 of this device is constituted of a microscopically porous and gas permeable layer 32 of an oxygen ion conductive solid electrolyte, a shield layer 38, a thin reference electrode layer 34 sandwiched between the solid electrolyte layer 32 and the shield layer 38, and a gas permeably porous measurement electrode layer 36 formed on the outer side of the solid electrolyte layer 32. A DC power supply 24 is connected to the two electrode layers 34 and 36 of the probe 30 to force a constant current to flow through the solid electrolyte layer 32 between the two electrode layers 34 and 36. The following explanation is made assuming that the current is made to flow from the measurement electrode layer 36 towards the reference electrode layer 34 as indicated by the arrow I. Usually the reference and measurement electrode layers 34 and 36 are both made of platinum which catalyzes oxidation reactions of HC and CO.

According to U.S. Pat. No. 4,207,159, a relatively large current is forced to flow between the two electrode layers 34 and 36. When the probe 30 is disposed in an engine exhaust gas, the exhaust gas diffuses to the reference electrode layer 34 through the porous layers 36 and 32. Because of the flow of the current from the measurement electrode 36 to the reference electrode 34, a portion of oxygen contained in the exhaust gas arriving at the reference electrode layer 34 is consumed in the formation of oxygen ions which migrate through the solid electrolyte layer 32 towards the measurement electrode layer 36. Therefore, an oxygen partial pressure at the surface of this electrode layer 34 becomes somewhat lower than an oxygen partial pressure at the measurement electrode layer 36, i.e., an oxygen partial pressure of $10^{-2}$ to $10^{-3}$ atm in the exhaust gas. Besides, HC and CO contained in the exhaust gas and diffused to the reference electrode layer 34 undergo oxidation reactions owing to the catalytic activity of this platinum electrode layer 34, resulting in further consumption of oxygen at this electrode layer 34. While the engine is operated with a rich mixture, the consumption of oxygen by the oxidation reactions is significant because of the presence of large amounts of HC and CO in the exhaust gas, so that the oxygen partial pressure at the reference electrode layer 34 lowers to a level of $10^{-15}$ to $10^{-30}$ atm. When the engine is operated with a lean mixture, the oxygen partial pressure at the reference electrode layer 34 becomes higher and nears the oxygen partial pressure in the exterior exhaust gas because of considerably decreased amounts of HC and CO in the exhaust gas and accordingly, considerably lessened consumption of oxygen for oxidation of HC and CO. Thus, a difference in oxygen partial pressure between the reference electrode layer 34 and the measurement electrode layer 36 becomes great in the case of using a rich mixture and becomes very small in the case of a lean mixture. The magnitude of an electromotive force the probe 30 generates is determined by the magnitude of the oxygen partial pressure difference between the two electrode layers 34 and 36 and, therefore, exhibits an abrupt change from a maximally large value to a negligibly small value, or reversely, when the air/fuel ratio varies across the stoichiometric ratio. Such a change in the magnitude of the electromotive force can be detected as a change in the output voltage $V_o$ of the DC power supply 24 which is supplying a constant current to the solid electrolyte layer 32 between the two electrode layers 34 and 36. The output voltage $V_o$ of the DC power supply 24 is varied so as to maintain the current I constant despite changes in the magnitude of the electromotive force E, so that the following equations hold:

$$I = (V_o - E)/R_e = \text{constant, hence, } V_o = E + IR_e$$

where $R_e$ represents the resistance of the solid electrolyte layer 32 between the two electrode layers 34 and 36. Thus, there is a linear relationship between the output voltage $V_o$ which can readily be measured and the electromotive force E generated by the probe 30.

According to U.S. Pat. No. 4,224,113, the intensity of the constant current I is made smaller than a certain critical current intensity. Therefore, ionization of oxygen at the reference electrode layer 34 becomes far less significant. While the engine is operated with a rich mixture, both the oxygen partial pressure at the reference electrode layer 34 and the oxygen partial pressure at the measurement electrode layer 36 are constantly as low as $10^{-10}$ to $10^{-30}$ atm because of the consumption of oxygen in catalytic oxidation reactions of large amounts of HC and CO, and the difference between these two oxygen partial pressures is too small to allow the probe 30 to generate an appreciable magnitude of electromotive force. When a lean mixture is supplied to the engine, the oxygen partial pressure at the measurement electrode layer 36 soon becomes practically equal to the oxygen partial pressure in the exhaust gas, meaning a rise to the level of a $10^{-2}$ to $10^{-3}$ atm, because of great decrease in the amounts of HC and CO to undergo catalytic oxidation reactions. However, the situation is different at the reference electrode layer 34. The oxygen partial pressure at this electrode layer 34 depends on the rate of diffusion of oxygen molecules through microscopic holes in the solid electrolyte layer 32, and the rate of diffusion is determined by the diameter and effective length of the individual holes besides the magnitude of oxygen partial pressure in the exhaust gas. Because of nonuniformity of the diameter and effective length of the holes in the solid electrolyte layer 32, relatively high oxygen partial pressures are developed in some areas of the reference electrode layer 34, considered microscopically, and relatively low oxygen partial pressures in other areas. Therefore, an oxygen partial pressure at the reference electrode layer 34 as an average value of the locally different values is considerably higher than the oxygen partial pressure at the measurement electrode layer 36 while the lean mixture is not greatly deviated from a stoichiometric mixture. Since the proportion of relatively high oxygen partial pressure areas in the reference electrode layer 34 increases as the air/fuel ratio of the lean mixture becomes higher, the difference in oxygen partial pressure between the reference electrode layer 34 and the measurement electrode layer 36 becomes gradually smaller, with a corresponding lowering in the magnitude of the electromotive force the probe 30 generates.

Figure 6:
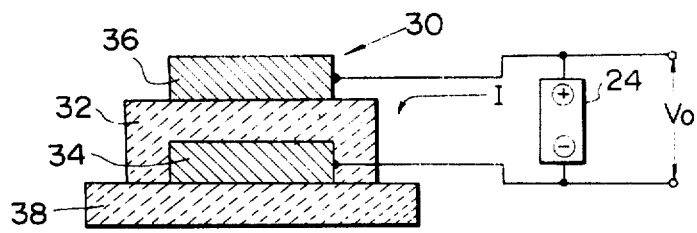
FIG. 6 shows schematically and sectionally a fundamental construction of an air/fuel ratio detecting device proposed prior to the present invention.
Figure 7:
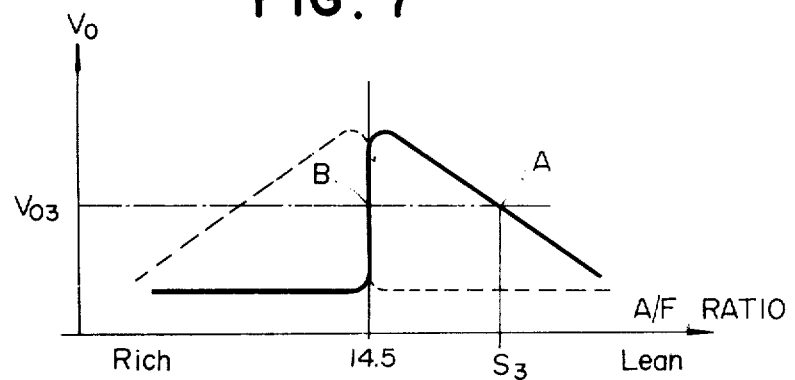
FIG. 7 is a graph for the explanation of the output characteristic of the device of FIG. 6 in an exhaust gas of an internal combustion engine.

Consequently, the relationship between the air/fuel ratio and the output voltage $V_o$ becomes as shown by solid line in FIG. 7 (when the direction of the flow of the current I is as illustrated in FIG. 6). In the case of a lean mixture, the output voltage $V_o$ has a proportional relation with the air/fuel ratio, but the output voltage $V_o$ falls abruptly to a negligibly low level upon arrival of the air/fuel ratio at the stoichiometric ratio. Therefore, an intermediate value $V_{o3}$ of the output voltage $V_o$ appears not only when the air/fuel ratio takes a value $S_3$ considerably higher than the stoichiometric ratio (at point A on the characteristic output curve) but also when the air/fuel ratio changes across the stoichiometric ratio (at point B on the output characteristic curve). As described hereinbefore, such indefiniteness of the indication becomes a matter of inconvenience in a practical air/fuel ratio control system. In FIG. 7, the curve in broken line represents an output characteristic of the device of FIG. 6 in the case of an adequately small current being made to flow from the reference electrode layer 34 towards the measurement electrode layer 36.

Figure 8:
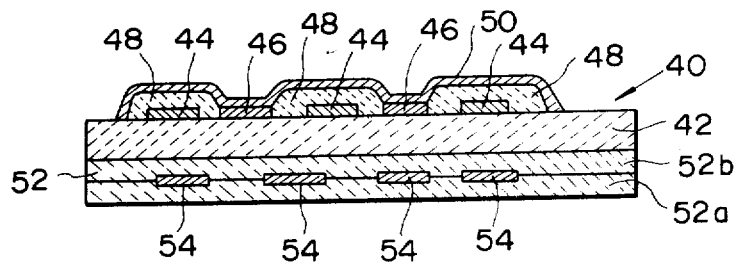
FIG. 8 shows schematically and sectionally an oxygen sensing element of an air/fuel ratio detecting device as another embodiment of the invention.

FIG. 8 shows an oxygen sensing element 40 as another embodiment of the present invention (a DC power source to be connected to this element 40 is omitted from this illustration), and FIGS. 9(A) to 9(F) illustrate a process of producing this element 40. This element 40 has a solid electrolyte layer 42, which is impermeable to gases, placed on a shield layer 52 which is made of a heat-resistant and electrically nonconducting material. On the outer side of the solid electrolyte layer 42, a reference electrode layer 44 of a catalytic material and a measurement electrode layer 46 of a noncatalytic material are formed so as to be spaced from each other. A porous and relatively thick gas-diffusion layer 48 is formed so as to cover the reference electrode layer 44, leaving the measurement electrode layer 46 uncovered, and a porous and relatively thin protective layer 50 is formed so as to cover not only the measurement electrode layer 46 but also the gas-diffusion layer 50. An electrical resistance heating element 54 is embedded in the shield layer 52.

Figure 9A:
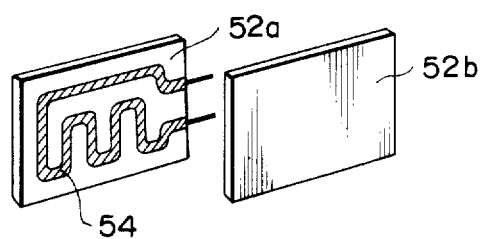
FIGS. 9(A) to 9(F) illustrate a process of producing the device of FIG. 8.
Figure 9B:
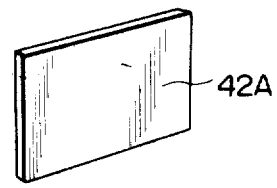
Figure 9C:
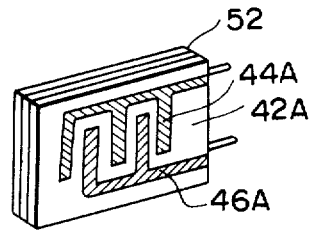
Figure 9D:
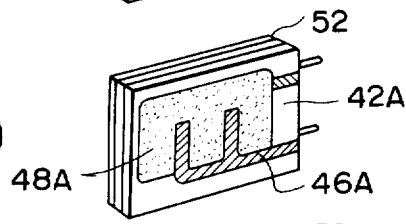
Figure 9E:
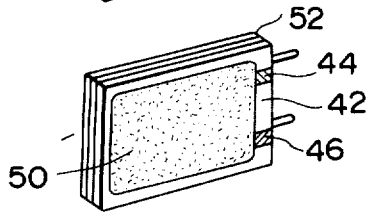
Figure 9F:
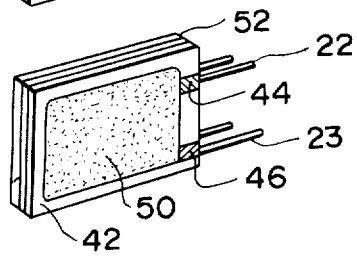

Referring to FIG. 9(A), the shield layer 52 is prepared by face-to-face bonding of two alumina sheets 52a and 52b. In advance, a paste containing a powdered conducting material such as platinum dispersed in an organic medium is applied onto one (52a) of the two alumina sheets in a suitable pattern as indicated at 54A by a screen-printing technique, followed by drying, so that an unfinished heater element 54A is sandwiched between the two alumina sheets 52a and 52b. Then a green (unfired) sheet 42A of a solid electrolyte material, shown in FIG. 9(B), is press-bonded to the assembly of the two alumina sheets 52a, 52b. Next, as shown in FIG. 9(C), a platinum paste is applied onto the outer surface of the unfired solid electrolyte sheet 42A by screen-printing to form an intermediate 44A of the reference electrode layer 44 in a comblike pattern, and a paste of a noncatalytic conducting material is printed onto the same surface of the solid electrolyte sheet 42A to form an intermediate 46A of the measurement electrode layer 46 in a comblike pattern. After drying of the printed pastes 44A and 46A, an alumina paste is applied onto the solid electrolyte sheet 42A by screen-printing, as indicated at 48A in FIG. 9(D), so as to cover the reference electrode layer intermediate 44A without covering the measurement electrode layler intermediate 46A, followed by drying. The resultant alumina layer 48A is an intermediate of the gas-diffusion layer 48. Then the unfinished element in the state of FIG. 9(D) is fired to achieve sintering of the respective sheets and printed layers. Thereafter, as shown in FIG. 9(E), the porous protective layer 50 is formed by plasma spraying so as to cover the sintered measurement electrode layer 46 and gas-diffusion layer 48. Finally lead terminals 22 and 23 are welded respectively to uncovered marginal regions of the reference and measurement electrode layers 44 and 46. It will be understood that this oxygen sensing element 40 exhibits the same output characteristic as the element 10 of FIG. 1 when disposed in a combustion gas and supplied with a constant DC current of an adequate intensity. By supplying a controlled heating current to the heater element 54, the temperature of this element 40 can be maintained at a constant and desirably high temperature even though the combustion gas undergoes changes in temperature. Since the internal resistance of the solid electrolyte layer 42 and gas diffusion constant of the gas-diffusion layer 48 depend on temperature, the maintenance of the element 40 at a constant temperature is effective for stable development of an output voltage accurately corresponding to a difference in oxygen partial pressure between the two electrode layers 44 and 46.

Figure 10:
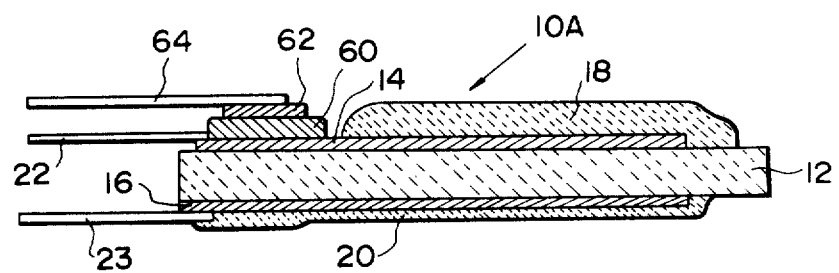
FIG. 10 shows schematically and sectionally an oxygen sensing element of an air/fuel ratio detecting device which is a modification of the device of FIG. 1.
Figure 11:
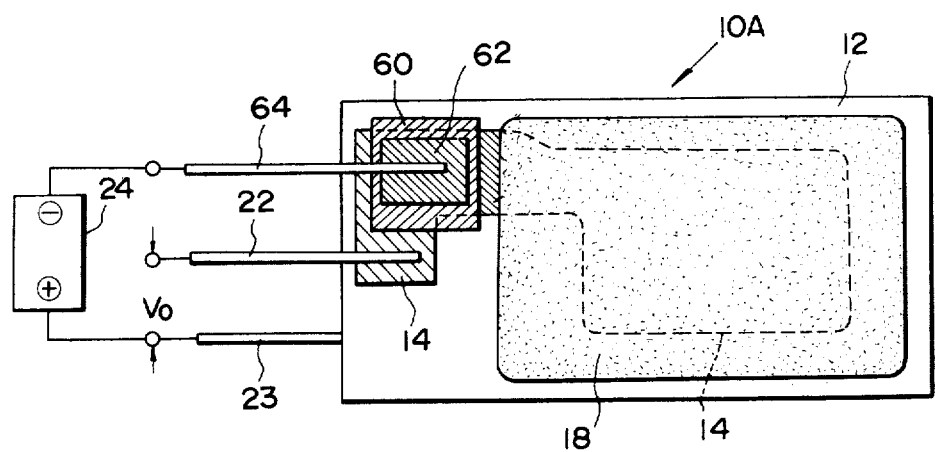
FIG. 11 is a plan view of the device of FIG. 10.

FIGS. 10 and 11 show another embodiment of the invention. An oxygen sensing element 10A in this embodiment is fundamentally similar to the element 10 of FIG. 1. As a sole difference, this element 10A has a temperature-sensitive resistance element 60 which is attached to an end part of the reference electrode layer 14, and a lead 64 is connected to an electrode 62 provided to this resistance element 60. The temperature-sensitive resistance element 60 is of the type having a tendency of lowering its resistance as the temperature lowers. In this case the constant current DC power supply 24 is connected to this lead 64 and the lead 23 which is connected to the measurement electrode layer 16, so that the resistance element 60, two electrode layers 14, 16 and solid electrolyte layer 12 are connected in series. The output voltage $V_o$ is measured between the leads 22 and 23 respectively connected to the reference and measurement electrode layers 14 and 16.

During use of the device of FIG. 1, the temperature-sensitive element 60 undergoes a change in its resistance as the temperature of the oxygen sensing element 10A varies such that the intensity of the current flowing through the solid electrolyte layer 12 is automatically regulated so as to compensate for a fluctuation of the output voltage $V_o$ attributed to changes in the internal resistance of the solid electrolyte layer 12 and gas diffusion constant of the gas-diffusion layer 18. Therefore, the temperature-sensitive element 60 is effective for stable developoment of an accurate output voltage by the oxygen sensing element 10A.

What is claimed is:

1. A device to detect an actual air/fuel ratio of an air-fuel mixture subjected to combustion in a combustor based on the magnitude of an oxygen partial pressure in a combustion gas which is exhausted from the combustor and which contains combustible substances, the device comprising:
   (i) an oxygen sensing element which is to be disposed in the combustion gas and comprises:
      (a) an oxgyen ion conductive solid electrolyte layer having a dense and gas impermeable structure,
      (b) a gas permeable porous first electrode layer which is formed on said solid electrolyte layer and comprised of a conducting and catalytic material which catalyzes oxidation reactions of combustible substances contained in the combustion gas,
      (c) a porous gas-diffusion layer formed on said first electrode layer, and
      (d) a gas permeable porous second electrode layer which is formed on said solid electrolyte layer so as to be spaced from said first electrode layer and made of a conducting material which does not catalyze said oxidation reactions;
   (ii) DC power supply means electrically connected to said first and second electrode layers of said oxygen sensing element for forcing a constant DC current to flow through said solid electrolyte layer between said first and second electrode layers, the intensity and the direction of flow of said constant current being determined such that an output voltage developed across said first and second electrode layers varies in dependence on the air/fuel ratio of an air-fuel mixture, from which the combustion gas is produced, when the air/fuel ratio varies on one side of the stoichiometric air/fuel ratio of said air-fuel mixture but remains substantially constantly at a maximal level when the air/fuel ratio varies on the other side of the stoichiometric ratio; and
   (iii) voltage-measuring means, electrically connected to said first and second electrode layers in parallel to said DC power supply means, for measuring the voltage produced across said first and second electrodes.

2. A device according to claim 1, wherein said DC power supply means (24) is connected to said oxygen sensing element (10) such that said constant current flows through said solid electrolyte layer (12) from said second electrode layer (16) towards said first electrode layer (14), so that said output voltage varies in dependence on the air/fuel ratio when the air/fuel ratio varies but remains above the stoichiometric ratio.

3. A device according to claim 1, wherein said DC power supply means (24) is connected to said oxygen sensing element (10) such that said constant current flows through said solid electrolyte layer (12) from said first electrode layer (14) towards said second electrode layer (16), so that said output voltage varies in dependence on the air/fuel ratio when the air/fuel ratio varies but remains below the stoichiometric ratio.

4. A device according to claims 1, 2, or 3, wherein said catalytic material for said first electrode layer comprises a (14) platinum group metal.

5. A device according to claim 4, wherein said platinum group metal comprises platinum.

6. A device according to claim 1, wherein said first and second electrode layers (14,16) are formed on two opposite sides of said solid electrolyte layer (12), respectively.

7. A device according to claim 1, wherein said first and second electrode layers (14,16) are formed on the same side of said solid electrolyte layer (12).

8. A device according to claim 7, wherein said oxygen sensing element (10) further comprises an electrical heating means (52,54) arranged to heat said solid electrolyte layer (12).

9. A device according to claim 1, wherein said oxygen sensing element (10) further comprises a temperature-sensitive resistance element (60) mounted on said solid electrolyte layer (12) and electrically connected to said first electrode layer (14) such that said DC power supply means (24) is connected to said first electrode layer via said resistance element (60), said resistance element being of the type having a tendency of lowering the electrical resistance thereof as the temperature lowers.

10. A device according to claim 1, wherein said oxygen sensing element (10) further comprises a gas permeable porous protective layer (20) formed on said solid electrolyte layer (12) so as to cover at least said second electrode layer (14).

11. A device according to claim 10, wherein said porous gas-diffusion layer and said gas permeable porous protective layer comprise alumina, spinel, magnesia or calcium zirconate. ($ZrO_2$—CaO).

12. A device according to claim 1, wherein said DC power supply means comprises means for providing the intensity of said constant current smaller than a critical current intensity above which said output voltage becomes substantially constant even though the air/fuel ratio varies on said one side of the stoichiometric ratio.

13. A device according to claim 1, wherein said oxygen ion conductive solid electrolyte layer comprises a metal oxide layer.

14. A device according to claim 13, wherein said oxygen ion conductive solid electrolyte layer comprises $ZrO_2$ stabilized with $Y_2O_3$, CaO or MgO; $Bi_2O_3$ stabilized with $Y_2O_3$ or $Nb_2O_5$; a $ThO_2$—$Y_2O_3$ system; or a CaO—$Y_2O_3$ system.

15. A device according to claim 13, wherein said oxygen ion conductive solid electrolyte layer consists essentially of said metal oxide layer.

16. A device according to claim 1, wherein said second electrode layer comprises a metal, SiC, an electronically conducting metal oxide or an oxide semi-conductor.

17. A device according to claim 16, wherein said metal comprises Au or Ag, said electronically conducting metal oxide comprises $SnO_2$, $V_2O_5$ or PbO or a mixture thereof with $Al_2O_3$ and said oxide semiconductor comprises $LaCrO_3$, $LaNiO_3$ or $SmCoO_3$ or a mixture thereof with Ca, Zr, Mg or Sr.

* * * * *